United States Patent
Yu

(10) Patent No.: US 11,602,325 B2
(45) Date of Patent: Mar. 14, 2023

(54) ULTRASONIC GUIDANCE OF SUBACROMIAL BURSA

(71) Applicant: Hsueh-Chih Yu, Taichung (TW)

(72) Inventor: Hsueh-Chih Yu, Taichung (TW)

( * ) Notice: Subject to any disclaimer, the term of this patent is extended or adjusted under 35 U.S.C. 154(b) by 285 days.

(21) Appl. No.: 15/908,871

(22) Filed: Mar. 1, 2018

(65) Prior Publication Data

US 2019/0269382 A1 Sep. 5, 2019

(51) Int. Cl.
*A61B 8/00* (2006.01)
*A61B 8/08* (2006.01)
*A61B 17/34* (2006.01)
*A61B 8/12* (2006.01)

(52) U.S. Cl.
CPC .......... *A61B 8/4245* (2013.01); *A61B 8/0841* (2013.01); *A61B 8/12* (2013.01); *A61B 17/3403* (2013.01)

(58) Field of Classification Search
CPC . A61B 8/4245; A61B 8/0841; A61B 17/3403; A61B 8/12
See application file for complete search history.

(56) References Cited

U.S. PATENT DOCUMENTS

2012/0310149 A1* 12/2012 Van Den Bossche ........................ A61M 1/0058
604/28

OTHER PUBLICATIONS

Peng, P.W.H, Subacromial Subdeltoid Bursa, 2015, Springer, Cham, Regional Nerve Blocks in Anesthesia and Pain Therapy, pp. 1-9 (Year: 2015).*
Tallia, Alfred, Diagnostic and Therapeutic Injection of the Shoulder Region, Mar. 15, 2003, American Family Physician, pp. 1-7 (Year: 2003).*
Gielen, JL, US and MRI shoulder us, Jun. 11, 2014, Universiteit Antwepen, pp. 14-16 (Year: 2014).*
Gupta et al, Normal Shoulder Ultrasound: Anatomy and Technique, 2015, Semin Musculoskelet Radiol; 19:203-211 (Year: 2015).*
Jane Moser, Information for you: Shoulder Impingement, Jan. 2004, Oxford Shoulder and Elbow Clinic, p. 1-7 (Year: 2004).*
Lee et al, Comprehensive Shoulder US Examination: A Standardized Approach with Multimodal Correlation for Common Shoulder Disease, 2016, RadioGraphics; 36:1606-1627 (Year: 2016).*

* cited by examiner

*Primary Examiner* — Rochelle D Turchen
(74) *Attorney, Agent, or Firm* — Alan D. Kamrath; Karin L. Williams; Mayer & Williams PC

(57) ABSTRACT

This invention provides an ultrasonic guidance method of subacromial bursa, which images subacromial bursa easily under ultrasound through specific positioning with patient's another hand appropriately pushing the elbow joint and allow needle insertion through near-end needle insertion from long axis of supraspinatus tendon. Moreover, the bursal fluid can be positional drained by the specific positioning and ultrasonic detector is moved to a sagittal plane around a greater tubercle of humerus for drawing bursal fluid through near-end needle insertion. As a result, in the invention, it is to medially rotate greater tubercle of humerus as possible to prevent lower margin of scapular bone from blocking the imaging of subacromial bursa and to allow SASD bursal fluid pooling near greater tubercle of humerus.

2 Claims, 20 Drawing Sheets

ULTRASONIC GUIDANCE OF SUBACROMIAL BURSA

TECHNICAL FIELD

The present invention relates to an ultrasonic guidance, and more particularly, to an ultrasonic guidance of subacromial bursa.

BACKGROUND

Ultrasound guided injection subacromial-subdeltoid bursa (SASD), or called as the subacromial bursa overlying rotator cuff muscle and tendon (mainly supraspinatus tendon) is widely applied in recent years. The major purpose of this technique is to draw the bursal fluid in subacromial bursa or to inject analgesic drugs into subacromial bursa, which alleviates severe pain produced in shoulders.

FIG. 1 is a structure diagram of subacromial bursa. Referring to FIG. 1, the subacromial bursa 1 is between the downside of scapular bone 2 and greater tubercle of the humerus 3. In order to detect the position of subacromial bursa 1, the doctor will ask the patient to put his/her hand in a position that the patient's ipsilateral hand is placed on the closest hip, just like putting the money in your pocket, where is known as modified Crass position. Referring to FIG. 2 and FIG. 3, in modified Crass position, the position of subacromial bursa 1 can be detected by a ultrasonic detector, then drawing of the bursal fluid in subacromial bursa or drugs injection can be processed.

However, modified Crass position used to detect the position of subacromial bursa 1 for drawing or injection has some problems in clinical cases listed as follows.

The subacromial bursa 1 tends to be blocked by acromion or greater tubercle of the humerus 3, and it causes the limitation of injecting angle, and is inclined to stab greater tubercle of the humerus 3 by mistake.

During injection or drawing, needle insertion can be divided into two types, near-end (cranial side) and far-end. Referring to FIG. 4, as for a far-end needle insertion, the convention detection method is known that the patient needs to shrink his/her neck and the needle tip should be turned upward for insertion. This posture makes both the doctor and the patient feel uncomfortable. In addition, the direction of far-end needle insertion is from bottom to top which makes the range of angle limited (less than 10 degrees.) When the inserting direction of needle is blocked by greater tubercle of the humerus 3, it is inclined to make a mistake to touch the greater tubercle of the humerus 3 by deeper insertion, or the needle may go into deltoid muscle only caused by shallow insertion angle.

Referring to FIG. 5, the direction of near-end (cranial side) needle insertion is from top to bottom. The subacromial bursa 1 tends to be blocked by bones below scapular bone 2, resulting in difficulties for needle insertion. In this situation, the direction of needle insertion will become steep which makes the needle uneasy to be imaged by ultrasonic probe.

The method of modified Crass position makes both the patient and the doctor feel uncomfortable and even tired during ultrasound-guided needle injection.

FIG. 6 is an ultrasonic image of subacromial bursa according to conventional modified Crass position method. Referring to FIG. 6, the thickness of subacromial bursa is about 0.4 cm, and the bursal fluid may not be drawn because of the incorrect data produced from ultrasonic images leading to no action in drawing fluids by the doctor using conventional modified Crass position method. As a result, since the fluid is not drained, the patient remains uncomfortable.

SUMMARY OF THE INVENTION

In summary, a conventional ultrasonic guidance method of subacromial bursa has its flaws. Therefore, the first purpose of this invention is to provide an ultrasonic guidance and an injection method of subacromial bursa. In this invention, a specific positioning is provided for keeping the ultrasonic probe parallel with ultrasound device (sonographic coronal plane) when ultrasonic probe is detecting or displaying. Based on this method, it is most appropriate for the doctor to insert needle and have subacromial bursa easily imaged.

The second purpose of this invention is to provide an ultrasonic guidance and injection method of subacromial bursa. In this invention, a specific positioning is provided to gather bursal fluid, and it is easy for the doctor to draw bursal fluid from near-end (cranial side) via positional drainage (pooling effect) of bursal fluid near the greater tubercle of the humerus 3.

The third purpose of this invention is to provide an ultrasonic guidance and injection method of subacromial bursa. In this invention, during needle insertion, a specific positioning can make humerus extremely medially rotate 180 degrees, (shoulder adduction plus forearm pronation) and a space is produced. Only deltoid muscle is in this space that makes needle insertion work smoothly. In addition, subacromial bursa will not be blocked by scapular bone lower margin, and subacromial bursa can be imaged easily.

To achieve the purposes, an ultrasonic guidance method of subacromial bursa is provided, the method at least comprises the following steps: (1) unfolding and extending a hand; (2) facing the palm of hand downward and rotating the hand toward abdomen; (3) holding the rotating side of elbow of hand by another hand; (4) moving to a sagittal plane around a greater tubercle of the humerus via a ultrasonic detector; and (5) imaging subacromial bursal in a display through the ultrasonic detector for drawing bursal fluid.

To achieve the purposes, an ultrasonic guidance method of subacromial bursa is provided, the method at least comprises the following steps: (1) unfolding and extending a hand; (2) facing the palm of hand downward and rotating the hand toward abdomen; (3) holding the rotating side of elbow of hand by another hand; (4) moving to a sagittal plane around a greater tubercle of the humerus via a ultrasonic detector; and (6) imaging subacromial bursal in a display through the ultrasonic detector for drawing bursal fluid; and (7) injecting through near-end (cranial side) needle insertion from long axis of supraspinatus tendon. The method may further include dislocating said greater tubercle of humerus and said subacromial bursa with an inserting angle over 15 degrees.

The advantages of this invention are summarized as follows:

Through the ultrasonic guidance of the specific positioning, the patient does not need to shrink his/her neck and the doctor does not bend over for detection. In other words, both the patient and the doctor feel comfortable under the ultrasonic detection and guidance of subacromial bursa.

When detecting the subacromial bursa via ultrasonic device, the specific positioning facilitates gathering of bursal fluid. In addition, precise imaging of ultrasonic device can help the doctor determine whether to draw bursal fluid or not.

The subacromial bursa blocked by bones below scapular bone can be avoided according to the specific positioning. In this situation, injection through near-end (cranial side) needle insertion from long axis of supraspinatus tendon has high accuracy which can be unrestrictedly operated by the doctor.

The remedy aimed to calcifying tendinitis of the supraspinatus tendon is effective in the invention. The injection in subacromial bursa under the condition of sonographic coronal plane enables the bursa to slightly stretch. As the result, the injecting angle of needle tip can be adjusted easily. Then, to and fro fenestration focusing on calcifying target can be processed.

A detailed description is given in the following embodiments with reference to the accompanying drawings.

BRIEF DESCRIPTION OF THE DRAWINGS

The components, characteristics and advantages of the present invention may be understood by the detailed descriptions of the preferred embodiments outlined in the specification and the drawings attached. Embodiments of the invention are illustrated by way of example, and not by way of limitation, in the figures of the accompanying drawings in which like reference numerals refer to similar elements.

DETAILED DESCRIPTION

Some preferred embodiments of the present invention will now be described in greater detail. However, it should be recognized that the preferred embodiments of the present invention are provided for illustration rather than limiting the present invention. In addition, the present invention can be practiced in a wide range of other embodiments besides those explicitly described, and the scope of the present invention is not expressly limited except as specified in the accompanying claims.

Referring to FIG. 7 to FIG. 11, the ultrasonic guidance method of subacromial bursa 100 is illustrated from step 110 to step 150 as follows.

Figure 1:
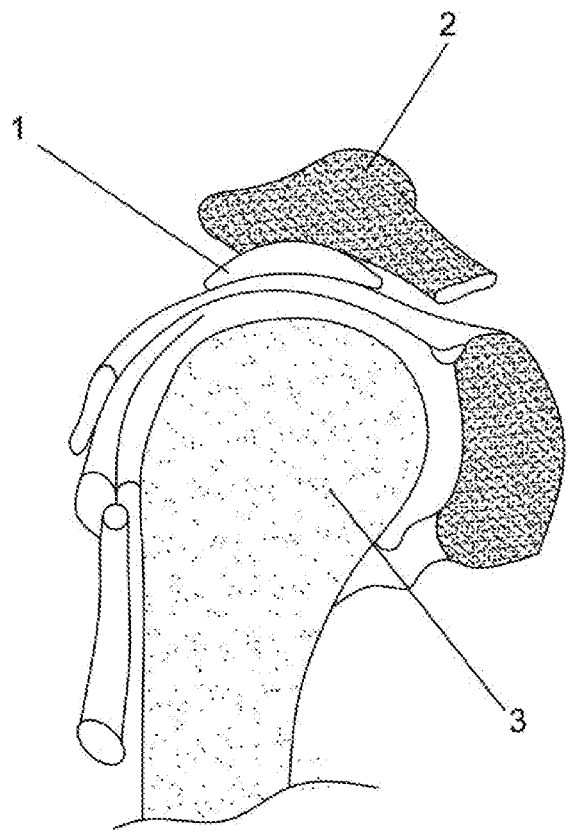
FIG. 1 is a structure diagram of subacromial bursa.
Figure 2:
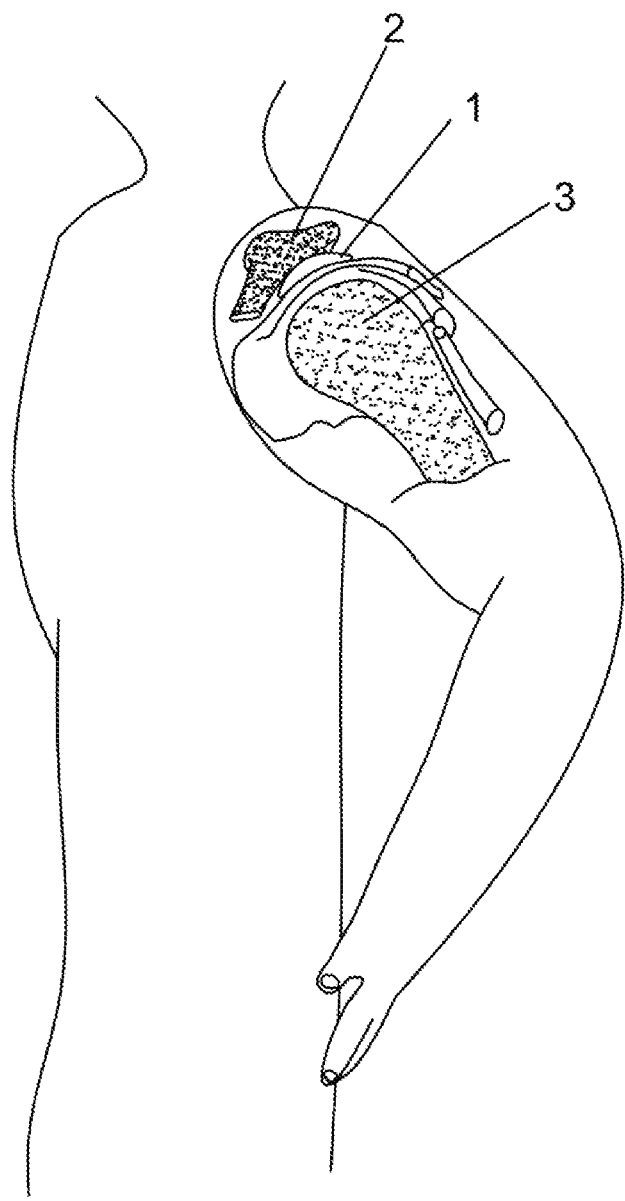
FIG. 2 is a schematic diagram of conventional modified Crass position.
Figure 3:
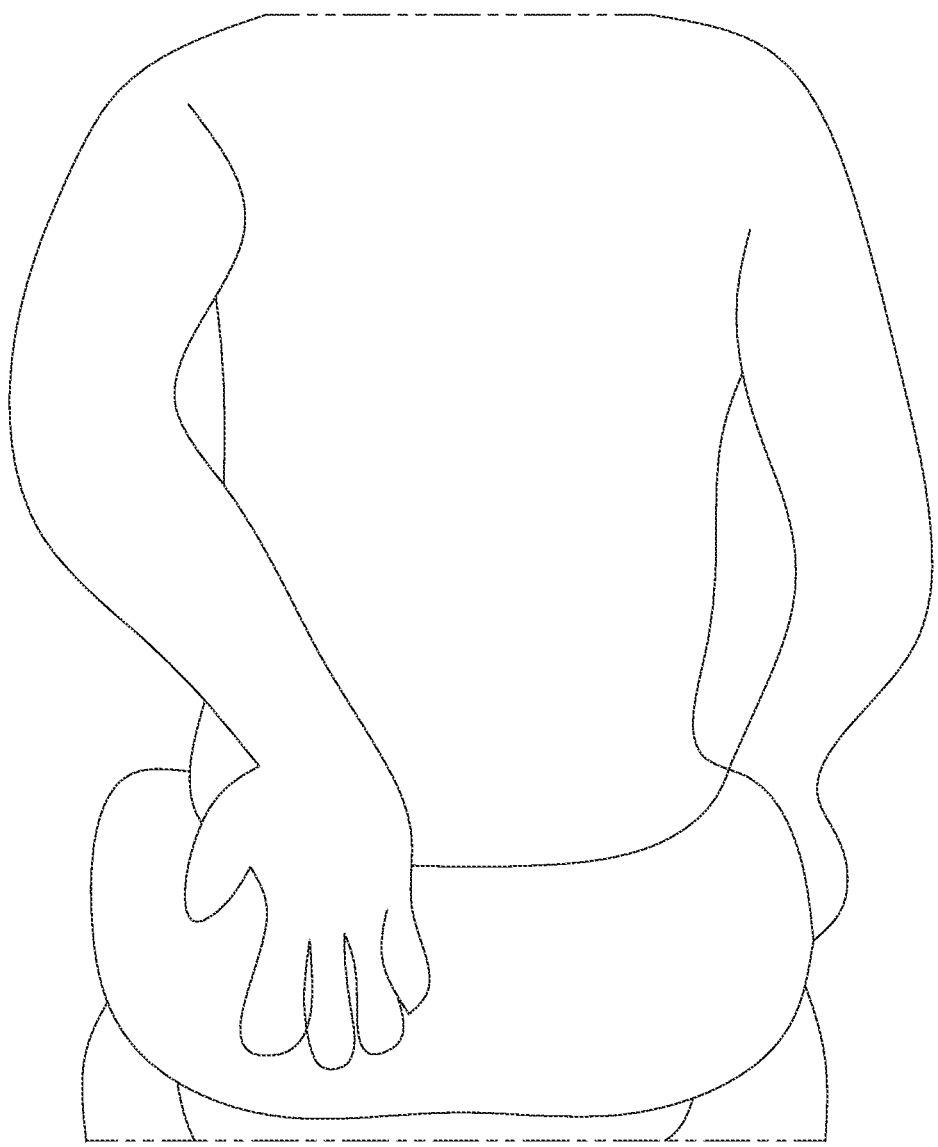
FIG. 3 is a demonstrative diagram of conventional modified Crass position.
Figure 4:
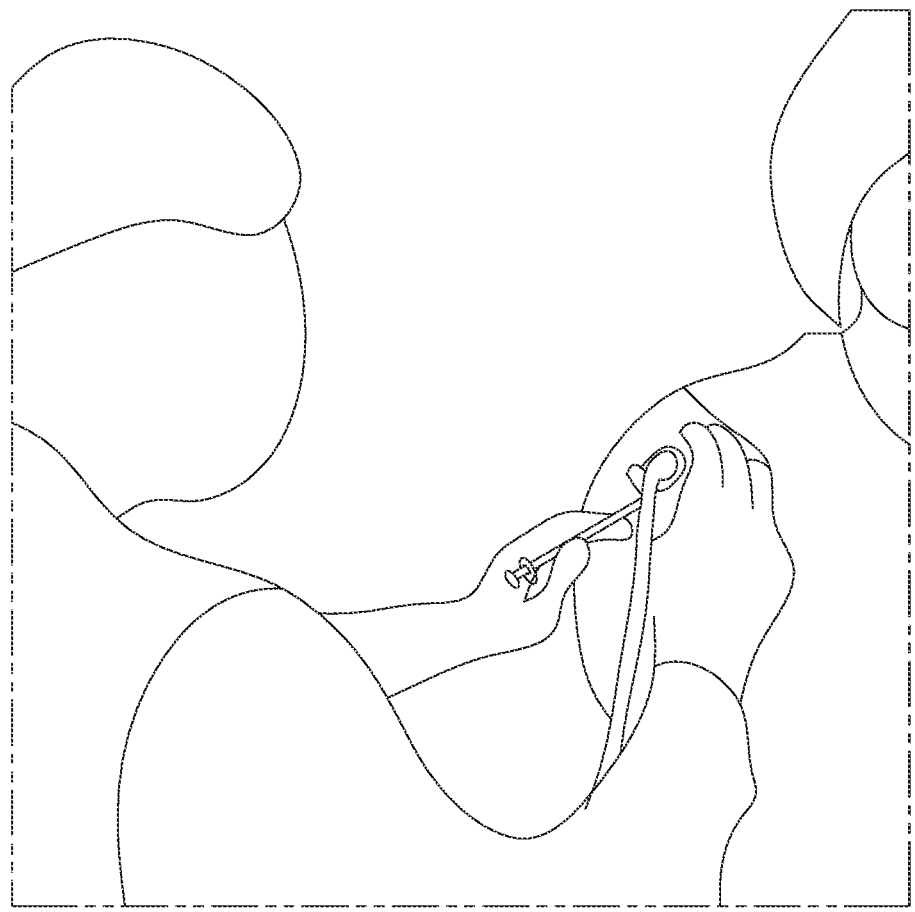
FIG. 4 is a far-end needle insertion view according to conventional modified Crass position.
Figure 5:
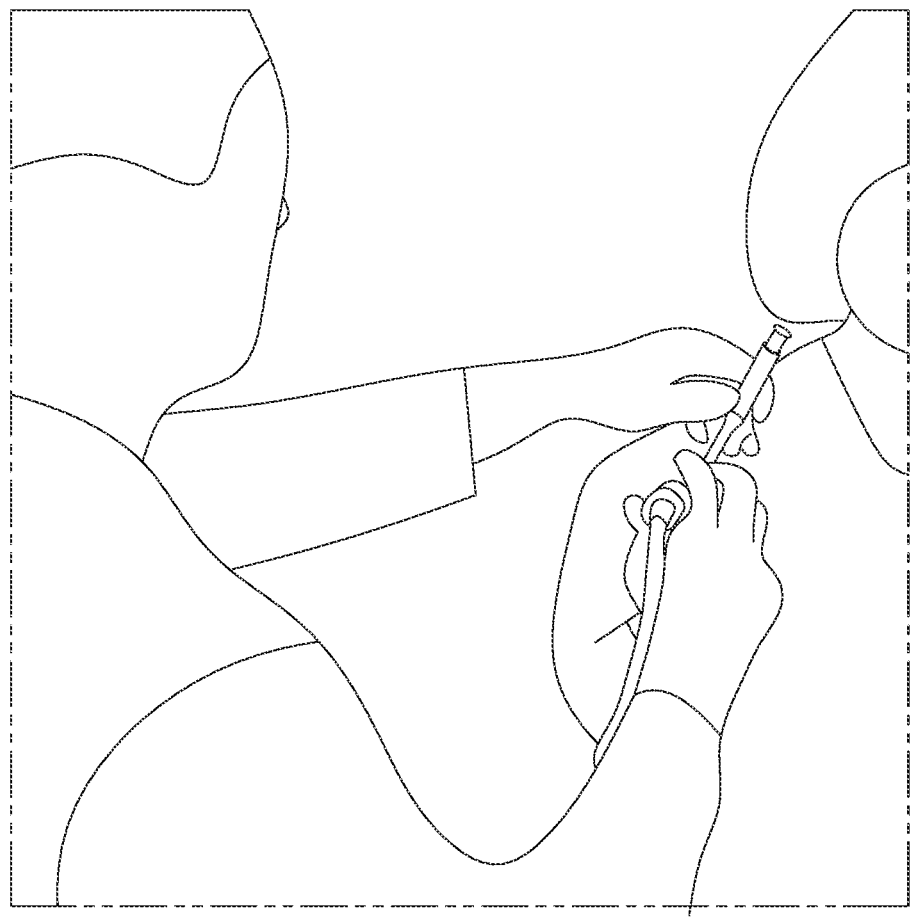
FIG. 5 is a near-end needle insertion view according to conventional modified Crass position.
Figure 6:
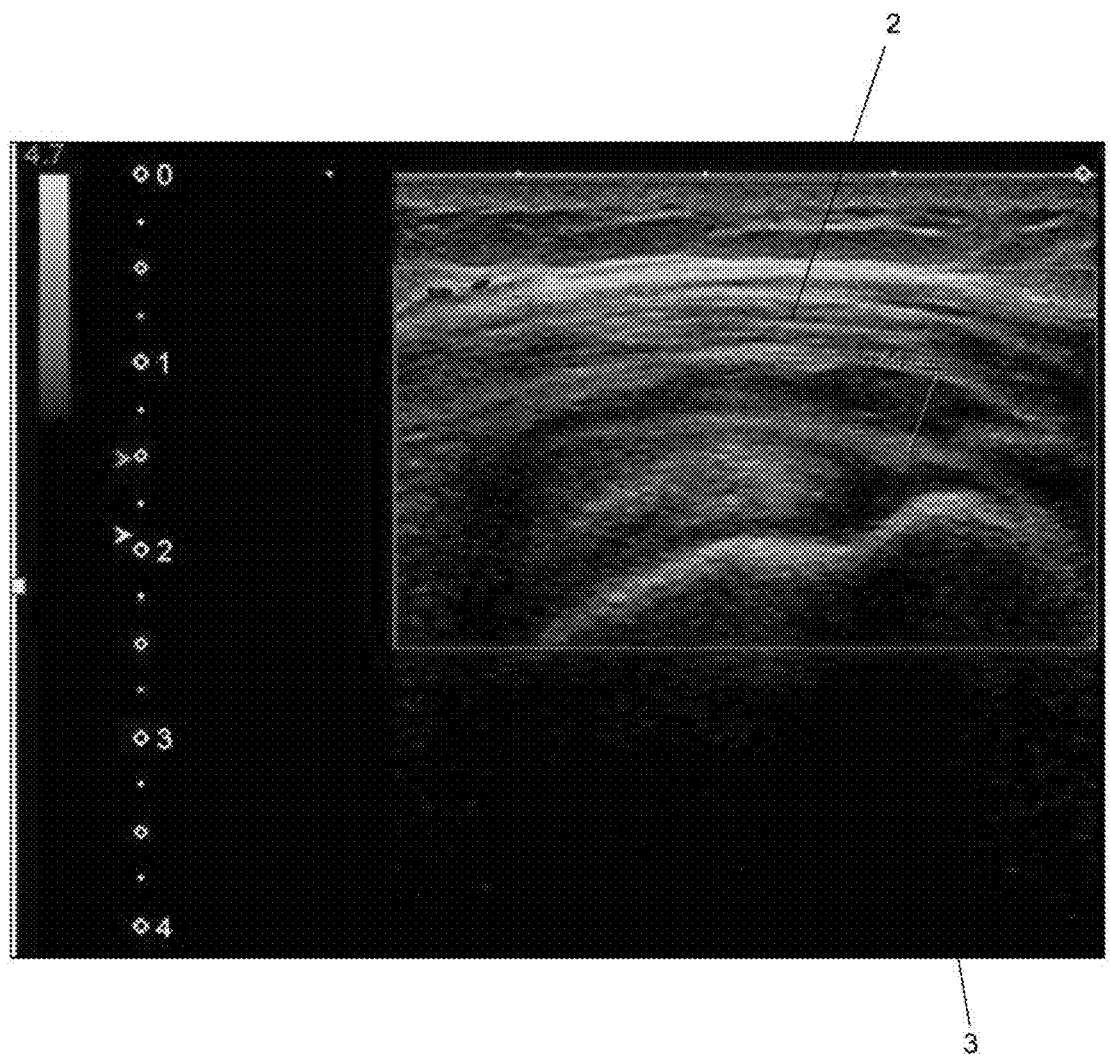
FIG. 6 is an ultrasonic image of subacromial bursa according to conventional modified Crass position method.
Figure 7:
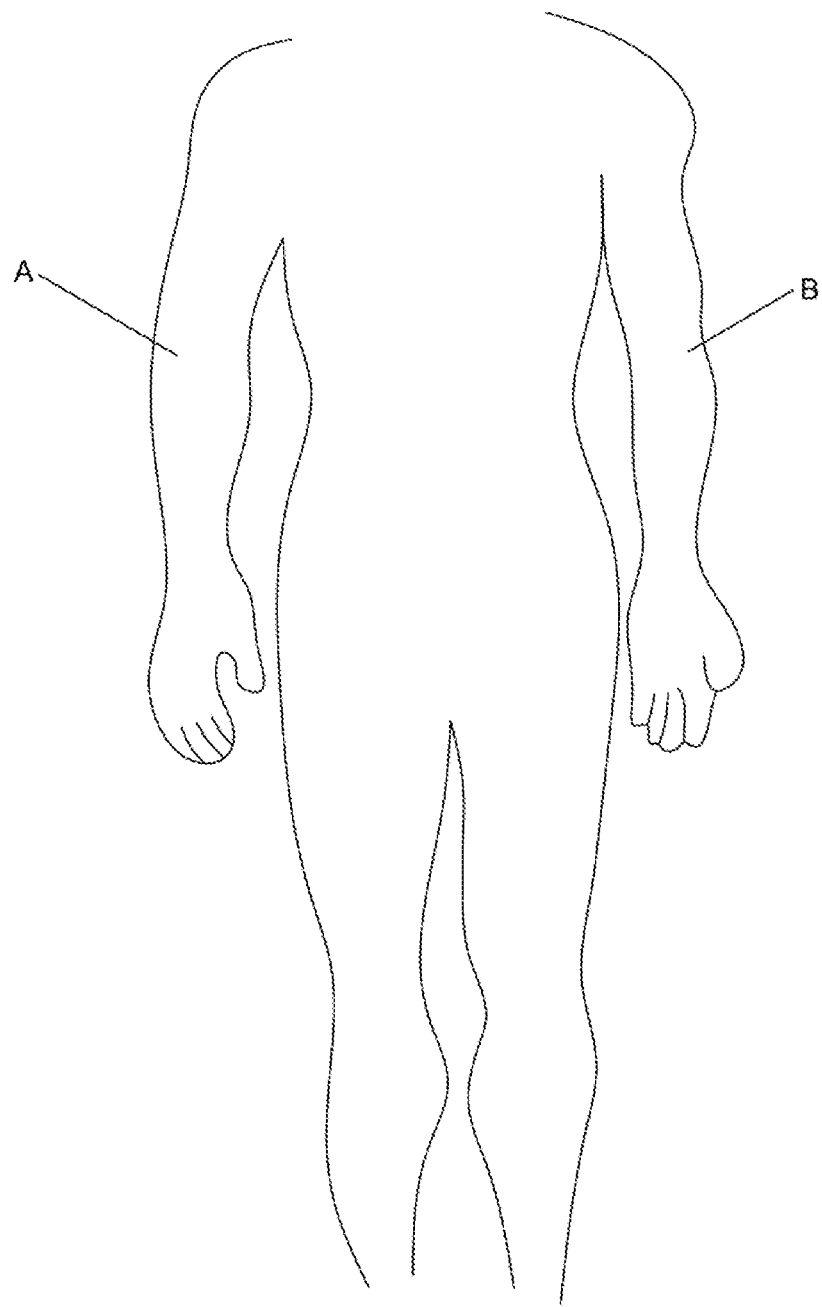
FIG. 7 is an example of an ultrasonic guidance method according to an embodiment of the invention.

FIG. 7 is an example of an ultrasonic guidance method according to an embodiment of the invention to show an unfolding state of patient's hand. Referring to FIG. 7, in step 110, a hand A is unfolded and extended.

Figure 8:
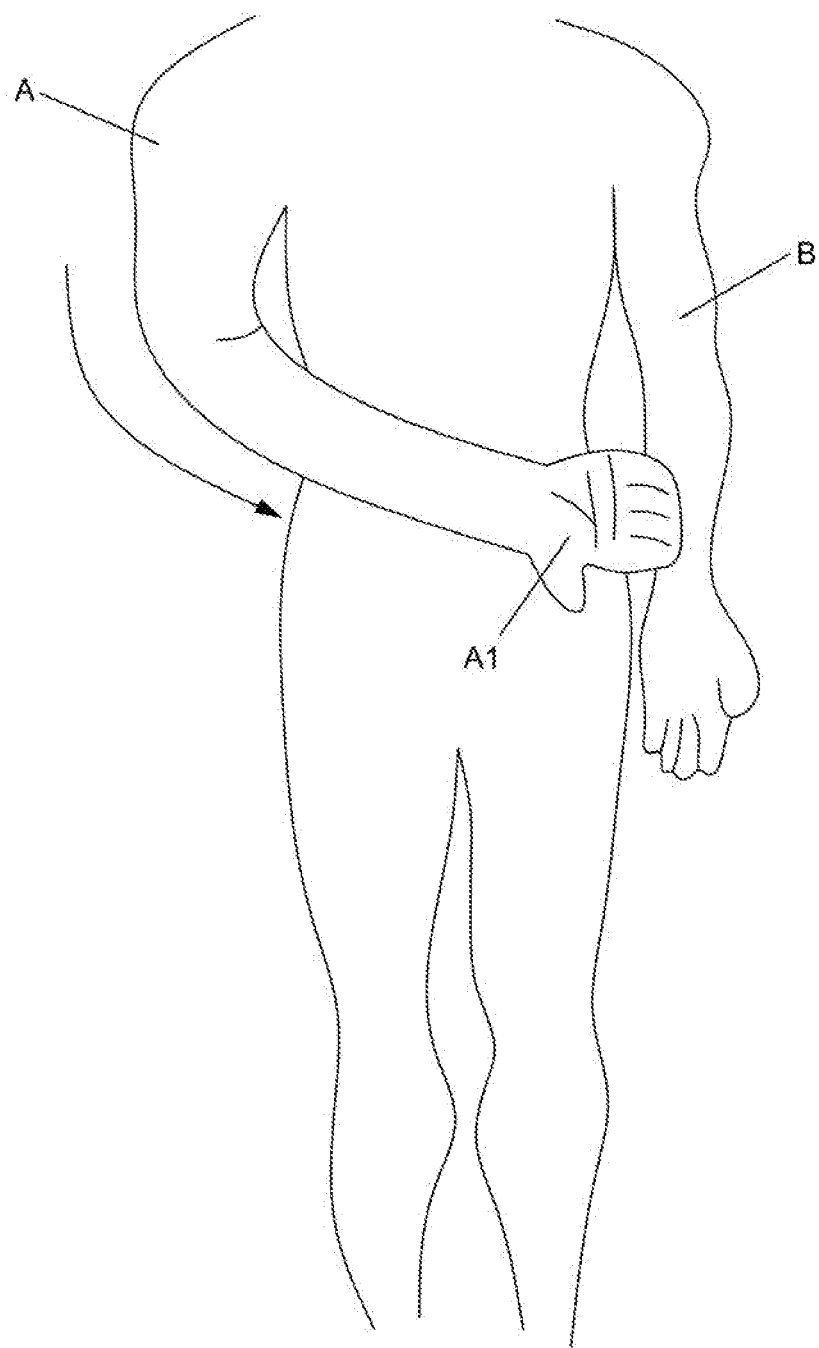
FIG. 8 is an example of an ultrasonic guidance method according to an embodiment of the invention.

FIG. 8 is an example of an ultrasonic guidance method according to an embodiment of the invention to show a rotating state of patient's arm. Referring to FIG. 8, in step 120, the palm A1 of hand faces downward and the arm of hand rotates toward abdomen.

Figure 9:
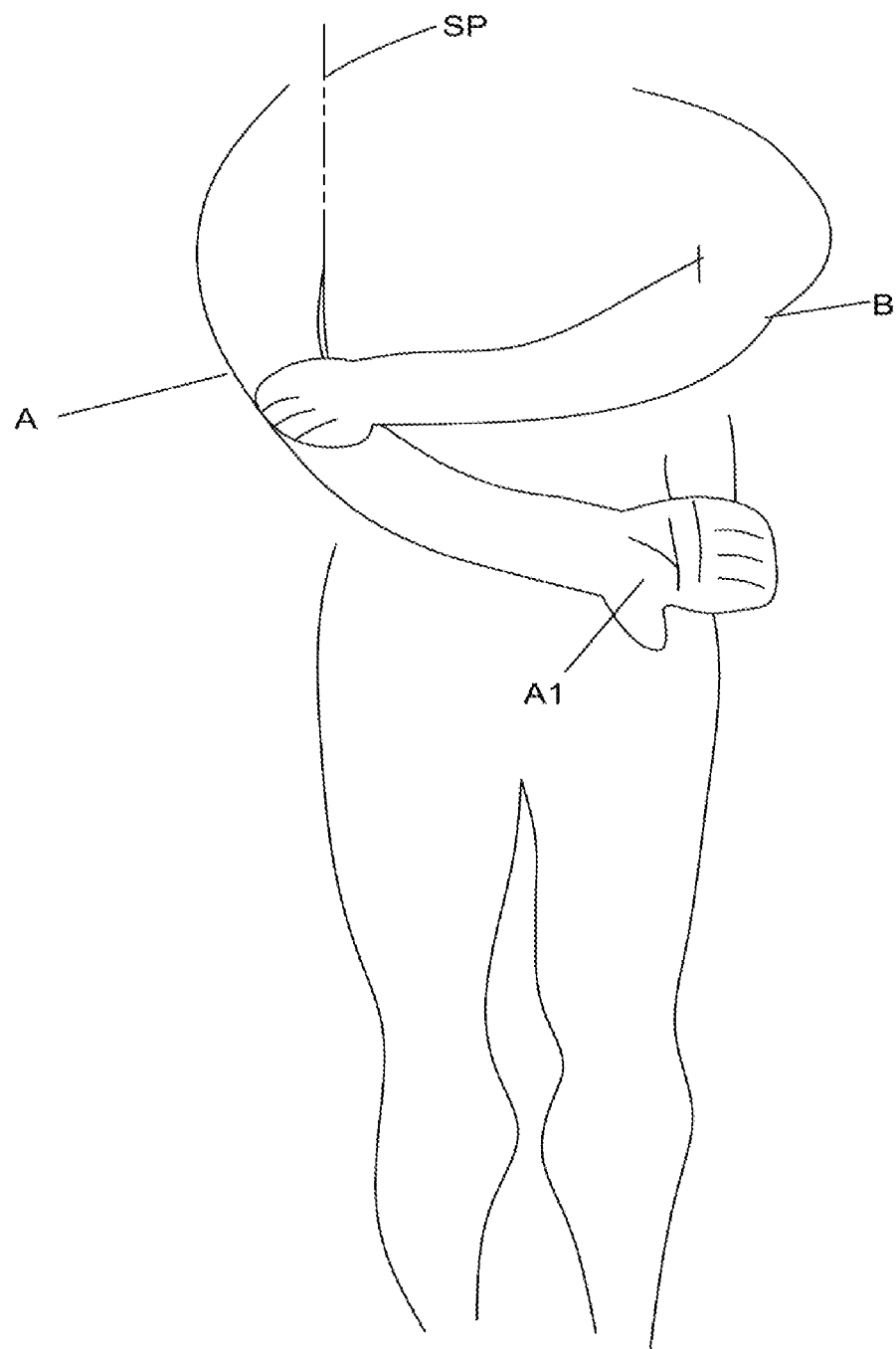
FIG. 9 is an example of an ultrasonic guidance method according to an embodiment of the invention.

FIG. 9 is an example of an ultrasonic guidance method according to an embodiment of the invention for showing the rotating side of elbow of hand is held by another hand. Referring to FIG. 8, in step 130, the rotating side of elbow (or elbow joint) of hand A is held by another hand B.

Figure 10:
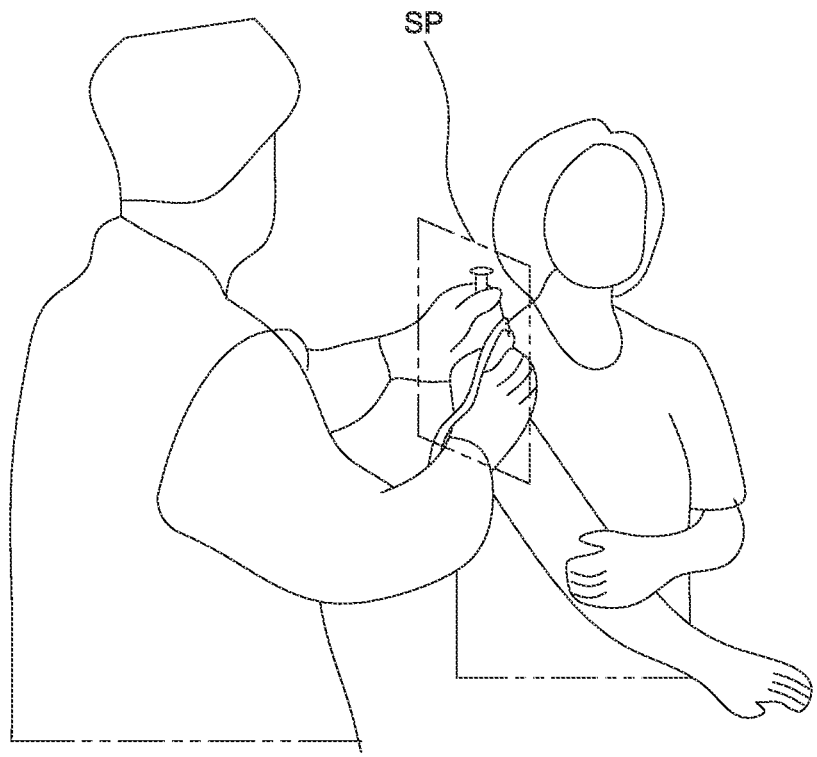
FIG. 10 is a demonstrative diagram of an ultrasonic guidance method according to an embodiment of the invention.
Figure 11:
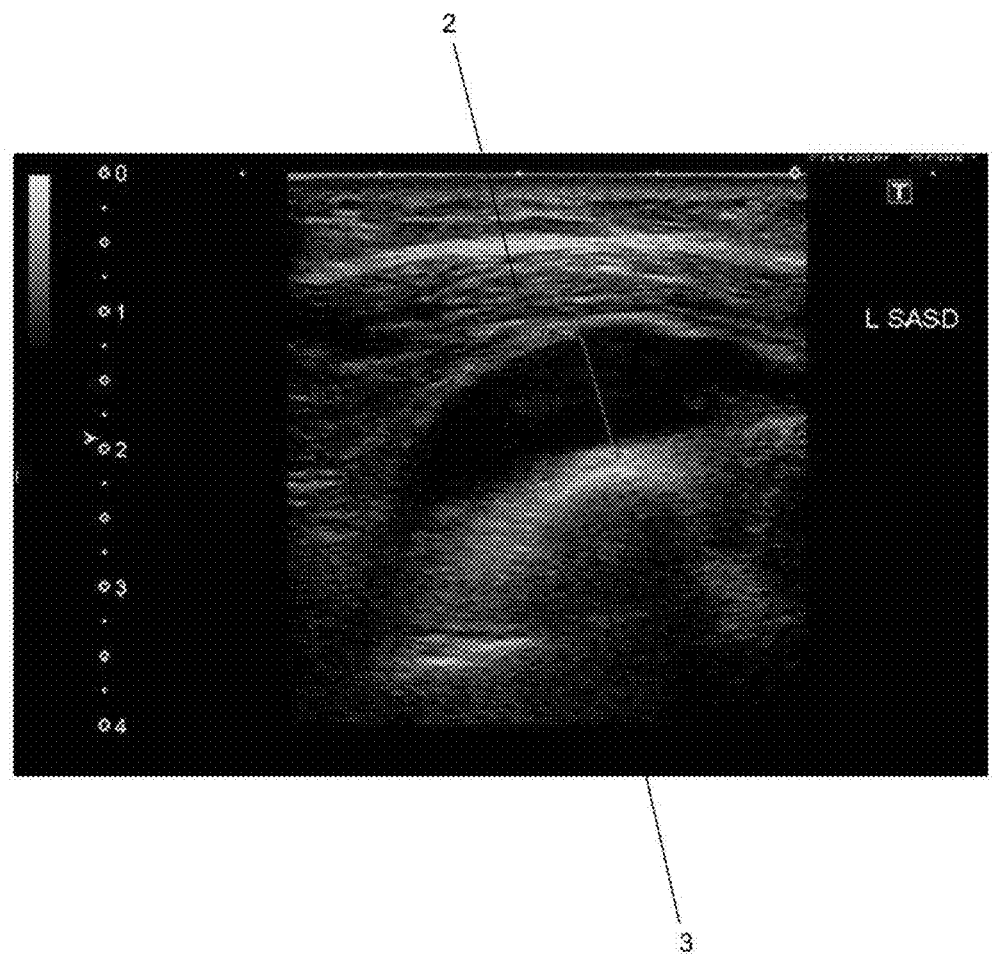
FIG. 11 is an ultrasonic image of ultrasonic guidance method according to an embodiment of the invention.

FIG. 10 is a demonstrative diagram of an ultrasonic guidance method according to an embodiment of the invention. FIG. 11 is an ultrasonic image of ultrasonic guidance method according to an embodiment of the invention. Referring to FIG. 10 and FIG. 11, in step 140, an ultrasonic detector moves to a sagittal plane SP around a greater tubercle of humerus 3.

Referring to FIG. 10 and FIG. 11, in step 150, a subacromial bursal 1 is imaged in a display through the ultrasonic detector for drawing bursal fluid.

Through step 100 to step 150, in one embodiment shown in FIG. 10, both the doctor and the patient can keep a normal sitting posture during the detection of subacromial bursal 1. Due to the medial rotation (shoulder adduction plus forearm pronation) of patient's greater tubercle of humerus 3, the location of subacromial bursal 1 can be detected by an ultrasonic device. Moreover, the specific positioning in the invention enable bursal fluid to be gathered in the subacromial bursal 1 (pooling effect.) Therefore, the subacromial bursal 1 can be precisely imaged in a display through the ultrasonic detection. The doctor can make a correct decision to determine whether to draw the bursal fluid or not. In general, the bursal fluid, less than 0.5 cm, will not be drawn. In the invention, the bursal fluid can be gathered and drawn.

In an embodiment, if it is inconvenient for the patient to rotate the arm, an alternative is applied. First, the hand A is extended, then rotate body of the patient toward the arm. Finally, another hand B holds the elbow (or elbow joint) of hand A to achieve the position shown in FIG. 7 to FIG. 10.

Referring to FIG. 11 to FIG. 15, an injection method for taping the effusion of SASD bursa is provided. The injection method comprises: (1) unfolding and extending a hand; (2) facing the palm of hand downward and rotating the hand toward abdomen; (3) holding the rotating side of elbow of hand by another hand; (4) moving to a sagittal plane SP around a greater tubercle of the humerus 3 via a ultrasonic detector; and (6) imaging subacromial bursal in a display through the ultrasonic detector; and (7) injecting through near-end (cranial side) needle insertion from long axis of supraspinatus tendon and moving to the sagittal plane SP around the greater tubercle of the humerus 3 via the ultrasonic detector, and the bursal fluid in subacromial bursal 1 outside the greater tubercle of humerus 3 is drawn.

Figure 12:
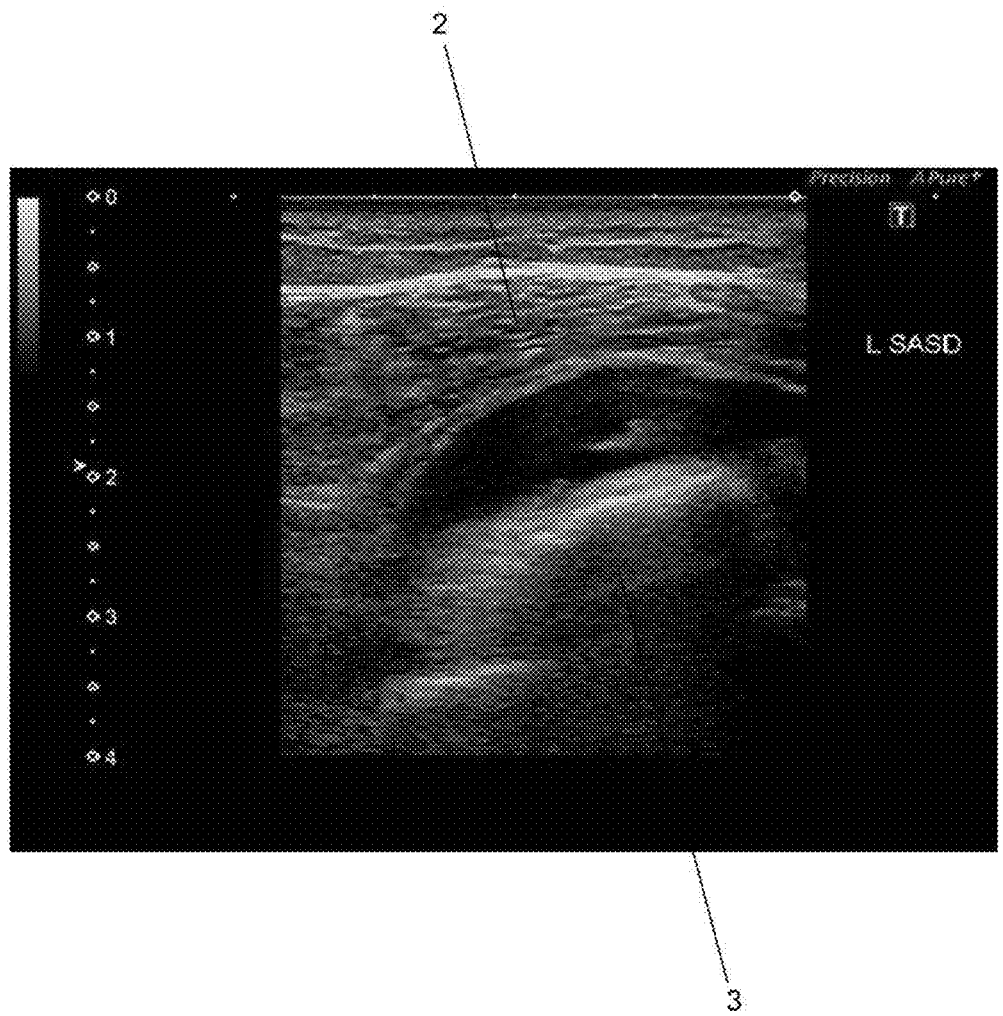
FIG. 12 is an ultrasonic image of near-end needle insertion in sagittal plane according to an embodiment of the invention.
Figure 13:
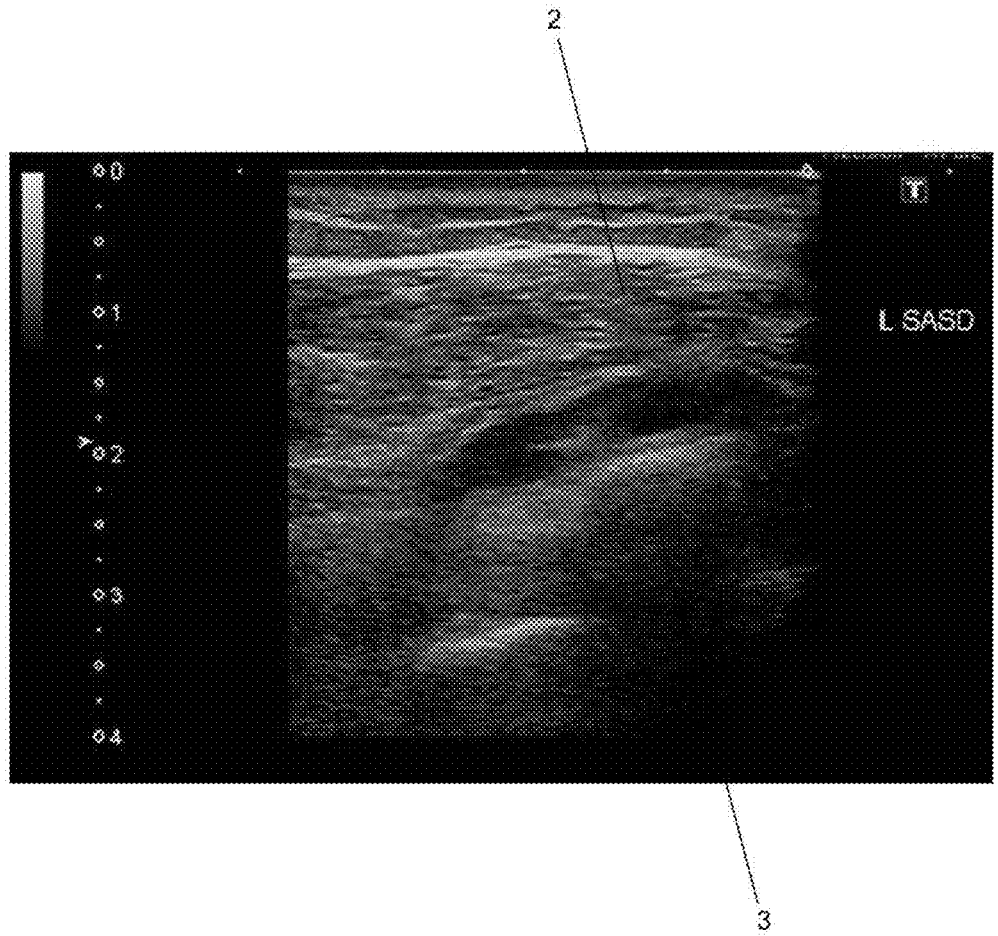
FIG. 13 is an ultrasonic image of drawing of fluid according to an embodiment of the invention.
Figure 14:
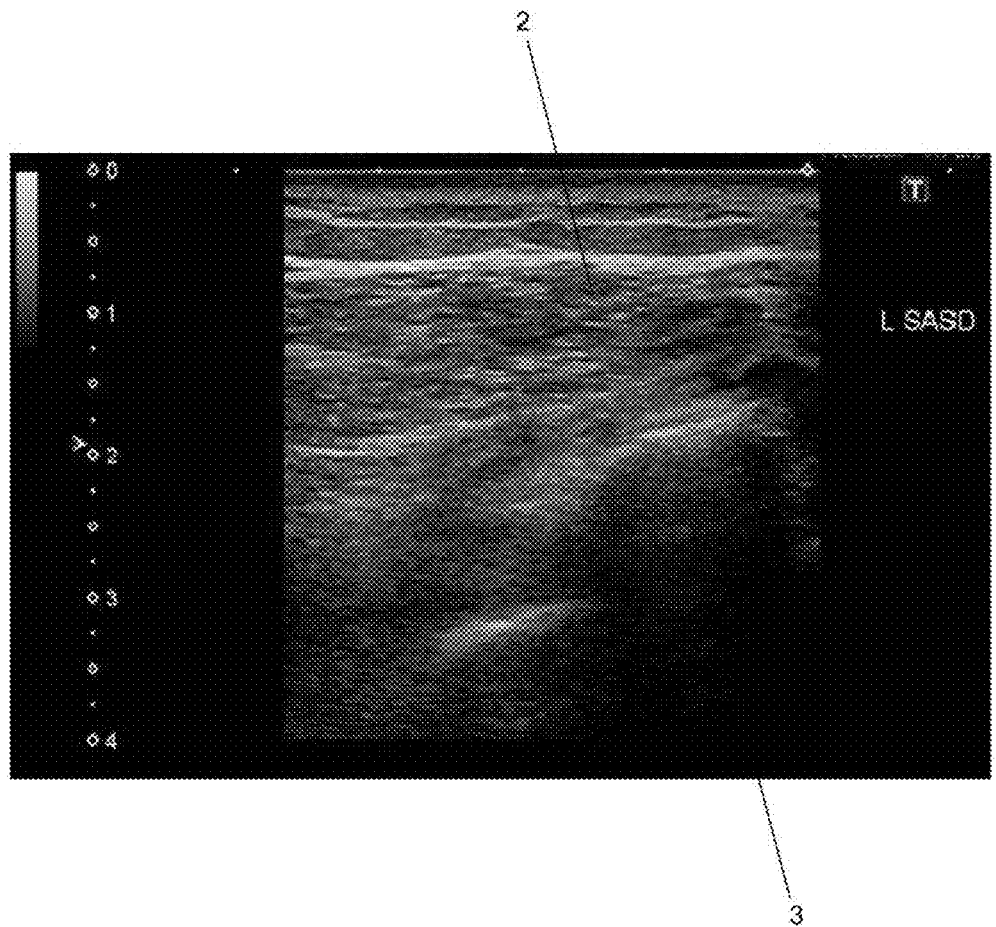
FIG. 14 is an ultrasonic image after drawing of drawing of fluid according to an embodiment of the invention.

Referring to FIG. 11 to FIG. 14, a drawing method of fluid in subacromial bursal 1 is provided. Referring to FIG. 11, in one embodiment, a specific positioning enables the bursal fluid to be gathered in subacromial bursal 1, and the bursal fluid is about 0.98 cm, shown in FIG. 11, to be drawn. Referring to FIG. 12, in one embodiment, injection through near-end (cranial side) needle insertion from long axis of supraspinatus tendon is implemented by the doctor, and the ultrasonic detector is moved to the sagittal plane SP. Referring to FIG. 11, in one embodiment, inserting needle will not be blocked by the scapular bone 2 during insertion. The doctor can adjust the inserting angle based on the location of bursal fluid. Referring to FIG. 13, in one embodiment, during the process of field drawing, the bursal fluid in the subacromial bursal 1 is gradually drawn by the doctor. The subacromial bursal 1 will recover its original size gradually after completely drawing the bursal fluid. Referring to FIG. 14, in one embodiment, the bursal fluid is drawn completely from the subacromial bursal 1. Hence, the patient's pain is alleviated. Moreover, injecting analgesic drugs into subacromial bursa 1 can increase the recovery.

Figure 15:
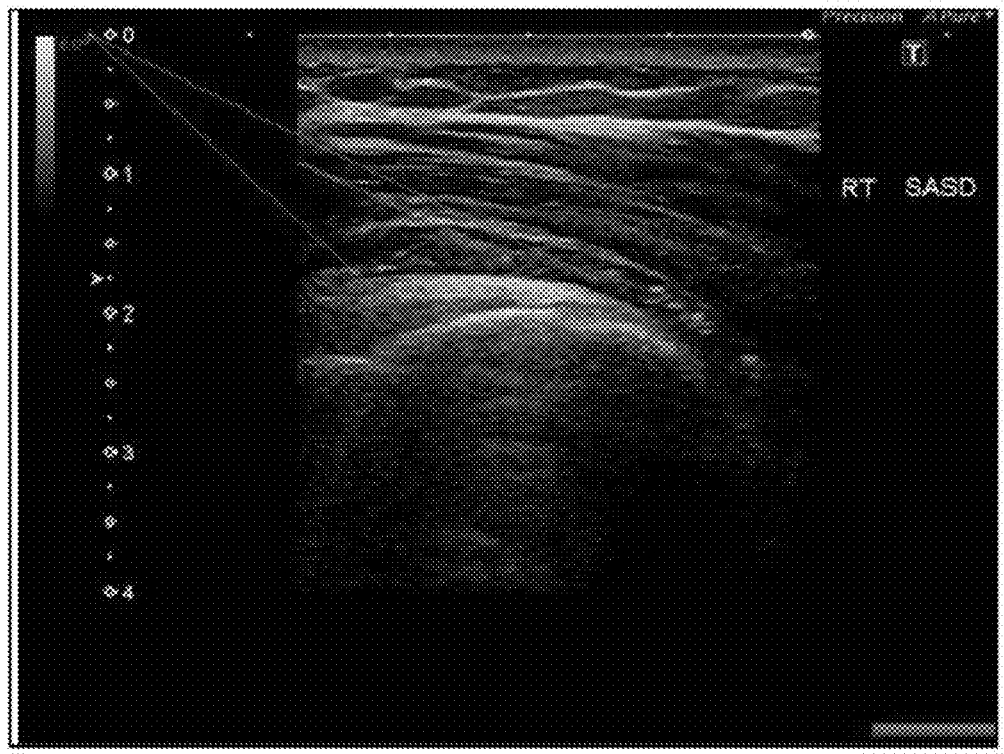
FIG. 15 is an example of inserting angle according to an embodiment of the invention.
Figure 16:
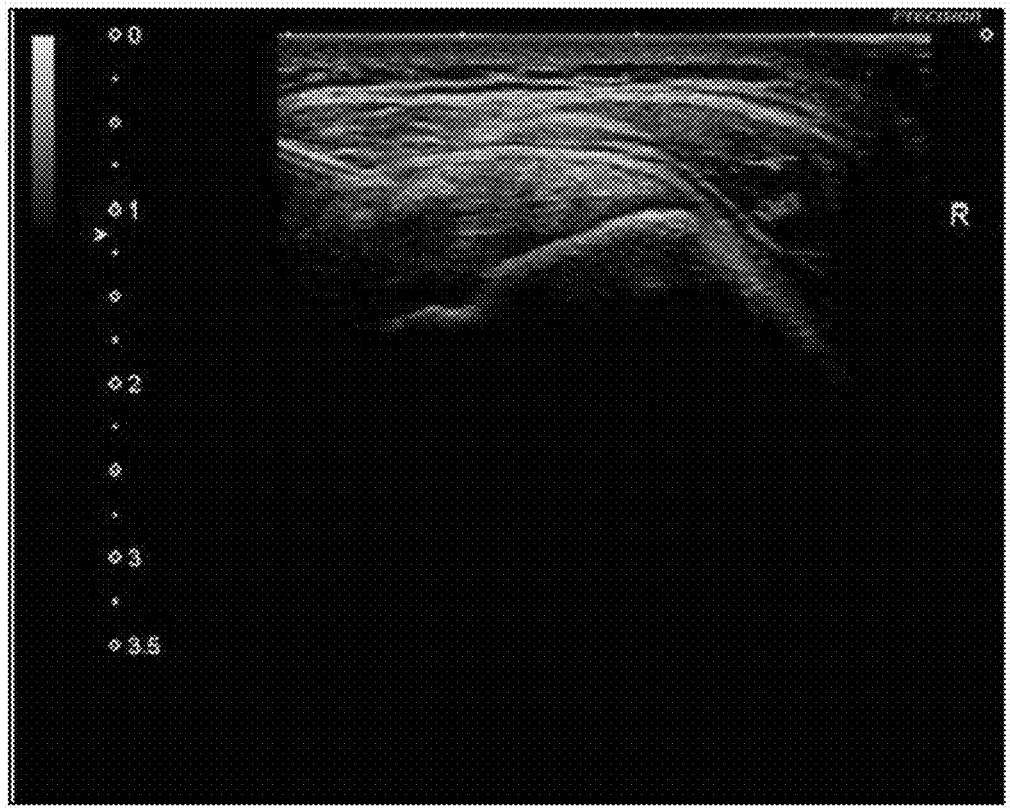
FIG. 16-20 are examples for ultrasound-guided injection for calcifying tendonitis of supraspinatus tendon.
Figure 17:
Figure 18:
Figure 19:

FIG. 15 is an example of inserting angle according to an embodiment of the invention. Referring to FIG. 15, the inserting direction and inserting location will not be blocked by the scapular bone 2 and the greater tubercle of humerus 3. Therefore, in the invention, the inserting angle over 15 degrees may be allowed, compared with the conventional technique with the inserting angle less than 10 degrees. The difficulty of needle insertion is minimized based on this method, and to cope with patient's pain by the doctor.

Referring to FIG. 10 to FIG. 15, in one embodiment, when the ultrasonic detector is moved to sagittal plane SP by the doctor, the detector and the image in the display are parallel. It is clear for the doctor to draw the fluid by needle insertion.

Figure 20:

FIG. 16 to 20 are ultrasonic images of subacromial bursa during injection according to an embodiment of the invention. Referring to FIG. 16 to 19, the remedy aimed to calcifying tendinitis of the supraspinatus tendon is effective in the invention. The injection in subacromial bursa under the sonographic coronal plane of ultrasonic device enables the bursa slightly to stretch. As the result, the injecting angle of needle tip can be adjusted easily. Then, to and fro fenestration focusing on calcifying target can be processed as shown in FIG. 20.

Many of the methods are described in their most basic form, but processes can be added to or deleted from any of the methods and information can be added or subtracted from any of the described messages without departing from the basic scope of the present invention. It will be apparent to those skilled in the art that many further modifications and adaptations can be made. The particular embodiments are not provided to limit the invention but to illustrate it. The scope of the embodiments of the present invention is not to be determined by the specific examples provided above but only by the claims below.

If it is said that an element "A" is coupled to or with element "B," element A may be directly coupled to element B or be indirectly coupled through, for example, element C. When the specification or claims state that a component, feature, structure, process, or characteristic A "causes" a component, feature, structure, process, or characteristic B, it means that "A" is at least a partial cause of "B" but that there may also be at least one other component, feature, structure, process, or characteristic that assists in causing "B." If the specification indicates that a component, feature, structure, process, or characteristic "may", "might", or "could" be included, that particular component, feature, structure, process, or characteristic is not required to be included. If the specification or claim refers to "a" or "an" element, this does not mean there is only one of the described elements.

An embodiment is an implementation or example of the present invention. Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. It should be appreciated that in the foregoing description of exemplary embodiments of the present invention, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims are hereby expressly incorporated into this description, with each claim standing on its own as a separate embodiment of this invention.

As will be understood by persons skilled in the art, the foregoing preferred embodiment of the present invention illustrates the present invention rather than limiting the present invention. Having described the invention in connection with a preferred embodiment, modifications will be suggested to those skilled in the art. Thus, the invention is not to be limited to this embodiment, but rather the invention is intended to cover various modifications and similar arrangements included within the spirit and scope of the appended claims, the scope of which should be accorded the broadest interpretation, thereby encompassing all such modifications and similar structures. While the preferred embodiment of the invention has been illustrated and described, it will be appreciated that various changes can be made without departing from the spirit and scope of the invention.

What is claimed is:

1. An ultrasonic guidance method of a subacromial bursa comprising steps of:
    unfolding and extending a hand of a patient;
    facing the palm of the hand downward and rotating the hand toward the abdomen;
    holding the rotating side of the elbow of the hand by another hand of the patient, thereby enabling bursal fluid to gather in the subacromial bursa;
    moving an ultrasonic detector to a sagittal plane around a greater tubercle of the humerus; and
    imaging a subacromial bursal in a display through said ultrasonic detector for drawing the bursal fluid,
    wherein said ultrasonic detector and an image in the display are parallel when the ultrasonic detector moves to the sagittal plane.

2. An injection method of subacromial bursa, said method comprising:
    unfolding and extending a hand;
    facing the palm of the hand downward and rotating the hand toward the abdomen;
    holding the rotating side of the elbow of the hand by another hand;
    moving an ultrasonic detector to a sagittal plane around a greater tubercle of the humerus;
    imaging a subacromial bursal in a display through the ultrasonic detector for drawing bursal fluid;

injecting through near-end needle insertion from long axis of supraspinatus tendon, the ultrasonic detector moving to the sagittal plane;
drawing a bursal fluid in said subacromial bursal by an injecting needle; and
dislocating the greater tubercle of the humerus and the subacromial bursa, wherein a range of an inserting angle of the injecting needle in the step of drawing a bursal fluid is over 15 degrees,
wherein when the ultrasonic detector moves to the sagittal plane, the ultrasonic detector and an image in the display are parallel.

* * * * *